(12) United States Patent
Vermeersch

(10) Patent No.: US 9,023,064 B2
(45) Date of Patent: May 5, 2015

(54) LIGATOR AND METHOD OF OPERATING AND MANUFACTURING SAME

(71) Applicant: James Vermeersch, Grover, MO (US)

(72) Inventor: James Vermeersch, Grover, MO (US)

(73) Assignee: INX Medical, LLC, Wildwood, MO (US)

( * ) Notice: Subject to any disclaimer, the term of this patent is extended or adjusted under 35 U.S.C. 154(b) by 239 days.

(21) Appl. No.: 13/679,475

(22) Filed: Nov. 16, 2012

(65) Prior Publication Data

US 2014/0058410 A1 Feb. 27, 2014

Related U.S. Application Data

(60) Provisional application No. 61/560,644, filed on Nov. 16, 2011.

(51) Int. Cl.
*A61B 17/12* (2006.01)
*A61B 17/30* (2006.01)

(52) U.S. Cl.
CPC . *A61B 17/12013* (2013.01); *A61B 2017/12018* (2013.01); *A61B 2017/306* (2013.01)

(58) Field of Classification Search
CPC ............... A61B 17/12013; A61B 2017/12018; A61B 2017/306
USPC .................................................. 606/139, 140
See application file for complete search history.

(56) References Cited

U.S. PATENT DOCUMENTS

| | | | |
|---|---|---|---|
| RE24,419 E * | 1/1958 | Ziherl ............................ | 604/71 |
| 3,760,810 A | 9/1973 | Van Hoorn | |
| 4,493,319 A | 1/1985 | Polk et al. | |
| 5,158,563 A | 10/1992 | Cosman | |
| 5,203,863 A | 4/1993 | Bidoia | |
| 5,207,690 A | 5/1993 | Rohrabacher et al. | |
| 5,336,229 A * | 8/1994 | Noda ............................. | 606/144 |
| 5,681,328 A | 10/1997 | Lamport et al. | |
| 5,697,940 A | 12/1997 | Chu et al. | |
| 5,741,273 A | 4/1998 | O'Regan | |
| 5,788,715 A | 8/1998 | Watson, Jr. et al. | |
| 5,846,254 A | 12/1998 | Schulze et al. | |
| 6,099,535 A | 8/2000 | Lamport et al. | |
| 6,974,466 B2 | 12/2005 | Ahmed et al. | |

(Continued)

FOREIGN PATENT DOCUMENTS

| | | |
|---|---|---|
| EP | 1339330 B1 | 8/2007 |
| WO | 9619145 A1 | 6/1996 |

(Continued)

OTHER PUBLICATIONS

International Search Report and Written Opinion, Application No. PCT/US13/69834, dated Jan. 30, 2014, p. 14.

*Primary Examiner* — Jonathan W Miles
*Assistant Examiner* — George J Ulsh
(74) *Attorney, Agent, or Firm* — Stinson Leonard Street LLP

(57) ABSTRACT

A device for discharging at least one band onto a tissue is provided. The device includes a housing; a suction assembly coupled to said housing; a dispensing assembly coupled in flow communication to said suction assembly; a discharge assembly coupled in flow communication to said dispensing assembly; and a first manual actuator coupled to said suction assembly and configured to move said suction assembly between a retracted position and an extended position wherein said suction assembly, in said retracted position, is configured to draw the tissue into said discharge assembly.

16 Claims, 11 Drawing Sheets

(56) References Cited

U.S. PATENT DOCUMENTS

| | | |
|---|---|---|
| 7,150,752 B2 | 12/2006 | Suzuki et al. |
| 7,189,247 B1 | 3/2007 | Zirps et al. |
| 7,488,333 B2 | 2/2009 | Ghareeb |
| 8,518,056 B2 * | 8/2013 | Smith .................. 606/140 |
| 2006/0259042 A1 | 11/2006 | Ali Hassanien |
| 2008/0319266 A1 | 12/2008 | Poll et al. |
| 2009/0182350 A1 | 7/2009 | McGown |
| 2010/0063517 A1 | 3/2010 | Cleator |
| 2010/0168520 A1 | 7/2010 | Poll et al. |
| 2010/0234859 A1 | 9/2010 | Bastia |
| 2010/0234949 A1 | 9/2010 | Bastia |
| 2011/0077666 A1 | 3/2011 | McCahon et al. |

FOREIGN PATENT DOCUMENTS

| | | | | |
|---|---|---|---|---|
| WO | WO99/65400 | * | 12/1999 | ............ A61B 17/12 |
| WO | 2011041069 A1 | | 4/2011 | |

* cited by examiner

LIGATOR AND METHOD OF OPERATING AND MANUFACTURING SAME

CROSS-REFERENCE TO RELATED APPLICATIONS

This application claims priority under 35 U.S.C. §119(e) of U.S. Provisional Patent Application No. 61/560,644 filed Nov. 16, 2011, in the name of the present inventor and entitled "Ligator and Method of Operating and Manufacturing Same", this provisional application being incorporated herein by reference.

BACKGROUND OF THE INVENTION

The present disclosure relates generally to tissue ligations, and more specifically, to methods and systems for dispensing bands onto tissue.

Physicians have used elastic ligating bands to treat lesions, including internal hemorrhoids and mucositis and for performing mechanical hemostasis. For ligating tissue inside a body cavity, an orifice, or a lumen, physicians often use a ligating device to access the target tissue and ligate the tissue. Conventionally, the physician may use the ligation device to position a stretched elastic band over the target tissue and then release the band onto the tissue so that the band contracts and catches the tissue.

The object of such ligation is to position the ligating band over the targeted lesion or blood vessel section of the tissue by first stretching the band beyond its undeformed diameter and then drawing the tissue to be ligated within the band. Thereafter, the band is released so that the band contracts around the tissue, applying inward pressure on the section of tissue caught within the band. The effect of the inward pressure applied by the band is to cut off blood circulation through the targeted tissue, thereby causing the tissue to die. The body then sloughs off the dead tissue, or the dead tissue may be aspirated into an aspirator.

In some hemorrhoid procedures, an anoscope is inserted into the anal cavity to visualize the hemorrhoids and to provide access to the hemorrhoids. Moreover, a relatively long forceps may be inserted into the anoscope to hold the hemorrhoid, which is pulled through an o-ring forceps with a relatively long arm. The external part of the o-ring holds an already stretched rubber band. Once the forceps has grasped the hemorrhoid, the rubber band is discharged from the o-ring by a simple pushing mechanism. Known procedures may require two people to perform the procedure, one person to hold an anoscope and the other person to apply the bands.

Because it is necessary to have two people to perform the technique, readjustment and re-firing are sometimes required. Sterilization of the equipment between patients is essential, so many sets are needed. Additionally, each patient may require multiple rubber bands to be applied to multiple hemorrhoids, wherein the o-ring must be loaded each time with a fresh band, which is a demanding and time consuming task. Thus, the o-ring forceps must be removed while maintaining the anoscope inside the patient, which can be painful to the patient to repeatedly remove and then reinsert the ligator device.

Some ligating devices may require a powered suction/vacuum system, such as a pneumatic pump, to draw the tissue within the device. Powered vacuum systems, however, are expensive to install and costly to maintain. Moreover, some health care facilities, such as doctor offices and/or out-patient care centers, may not be equipped with a powered vacuum system which limits and/or eliminates such tissue procedures care at such facilitates.

SUMMARY OF THE INVENTION

In one aspect, a device for discharging at least one band onto a tissue is provided. The device includes a housing; a suction assembly coupled to the housing; a dispensing assembly coupled in flow communication to the suction assembly; a discharge assembly coupled in flow communication to the dispensing assembly; and a first manual actuator coupled to the suction assembly and configured to move the suction assembly between a retracted position and an extended position wherein the suction assembly, in the retracted position, is configured to draw the tissue into the discharge assembly.

In another aspect, a device for discharging at least one band onto a tissue is provided. The device includes a housing; a suction assembly coupled to the housing; a dispensing assembly coupled in flow communication to the suction assembly; a discharge assembly coupled in flow communication to the dispensing assembly; a first actuator coupled to the suction assembly and configured to move the suction assembly between a retracted position and an extended position wherein the suction assembly, in the retracted position, is configured to draw the tissue into the discharge assembly; and a second actuator coupled to the dispensing assembly and configured to move the dispensing assembly between another retracted position and another extended position wherein the dispensing assembly, in the other extended position, is configured to dispense the at least one band along the discharge assembly and onto the tissue.

Still further in another aspect, a method of assembling a ligator device is provided. The method includes coupling a first actuator to said housing; coupling a suction assembly to the first actuator, the suction assembly being configured to move between a retracted position and an extended position; and coupling in flow communication a dispensing assembly to the suction assembly.

Although specific features of various embodiments may be shown in some drawings and not in others, this is for convenience only. Any feature of any drawing may be referenced and/or claimed in combination with any feature of any other drawing.

DETAILED DESCRIPTION OF THE INVENTION

The embodiments relate to the treatment of tissue by elastic band ligation (alternatively referred to as rubber band ligation). More particularly, the embodiments provide an elastic band ligation that is accurately positioned in the rectum by a single user for one-handed operation to facilitate application of one or more elastic bands to hemorrhoidal tissue. The embodiments described herein describe a self-contained, one-handed operated ligator device for ligating hemorrhoids. It should be understood that the embodiments described herein for ligator devices are not limited to hemorrhoids and should be further understood that the descriptions and figures that utilize hemorrhoids are exemplary only.

In the embodiments described herein, treatment of hemorrhoids by elastic band ligation facilitates placing an elastic band on tissue in the rectum above the area of the hemorrhoid where there is little sensation known as the dentate line. The tissue trapped in the band being cut off from its blood supply degenerates and is sloughed, and the elastic band along with the sloughed tissue is passed with bowel motions, the resulting healing process causes the tissue in the vicinity to become fixed and prolapse of the hemorrhoidal tissue is minimized. Furthermore, the elastic band ligation technique facilitates relieving hemorrhoidal symptoms.

Figure 1:
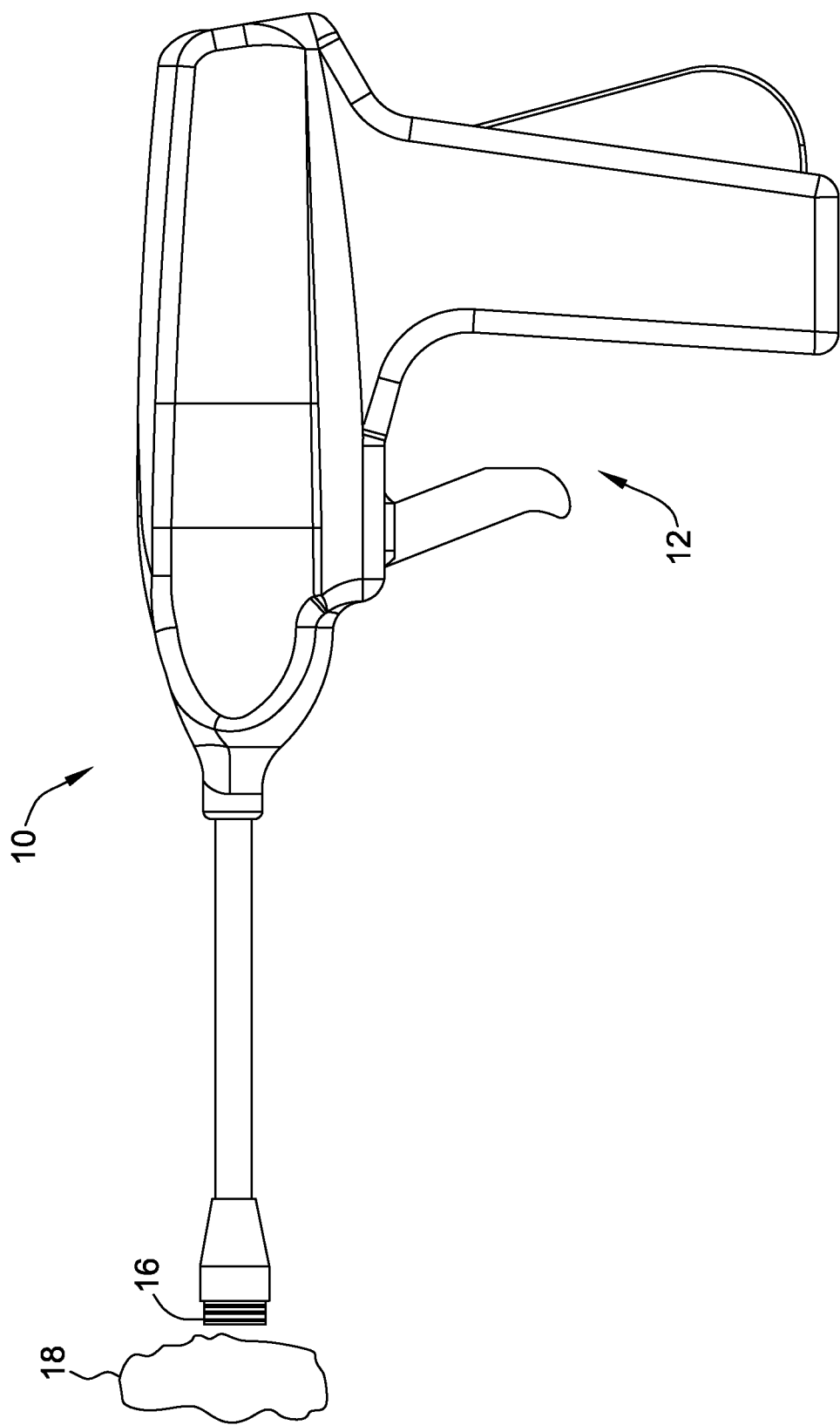
FIG. 1 is a side view of an exemplary ligator device in a first operating position.
Figure 2:
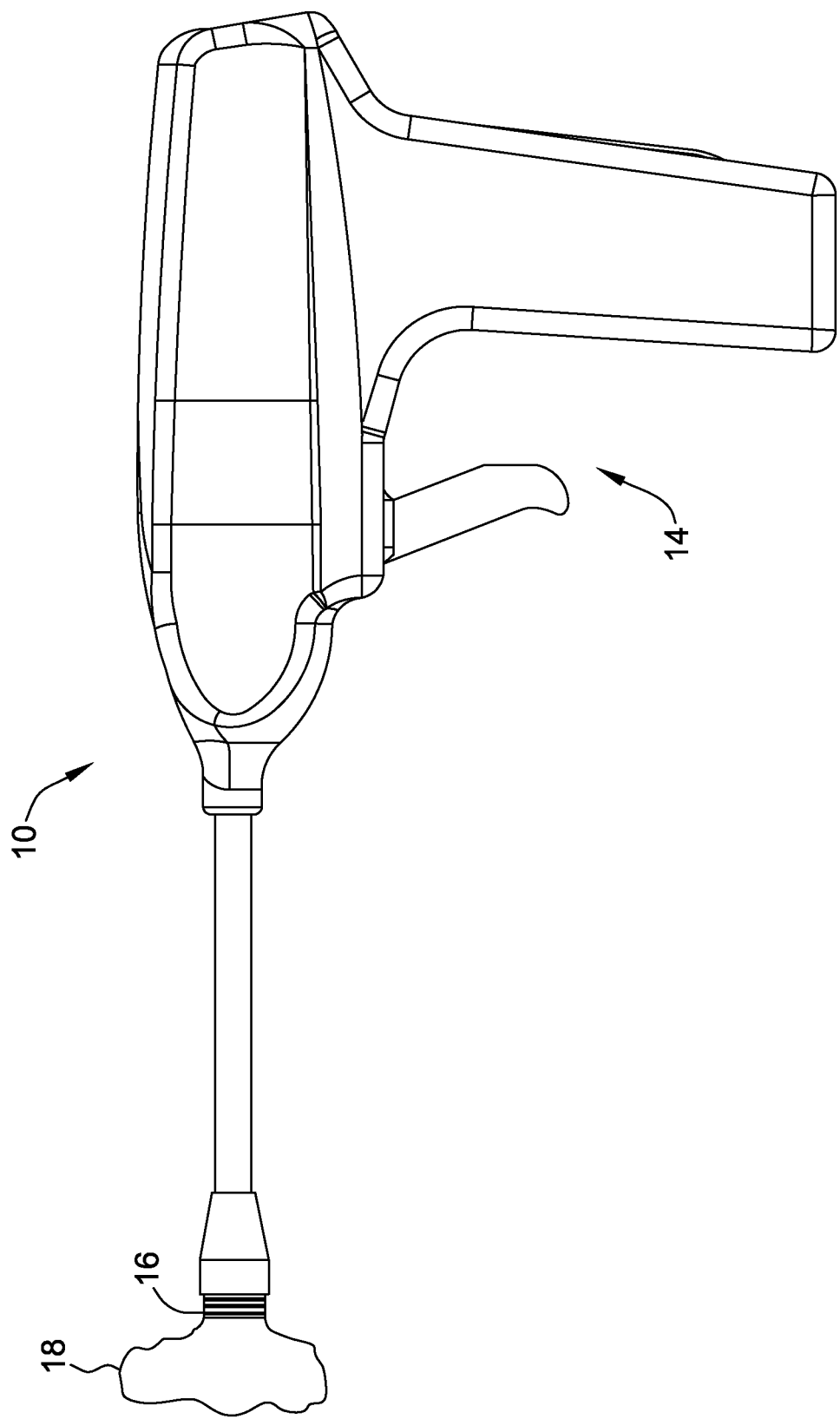
FIG. 2 is another side view of the ligator device shown in FIG. 1 in a second operating position.
Figure 3:
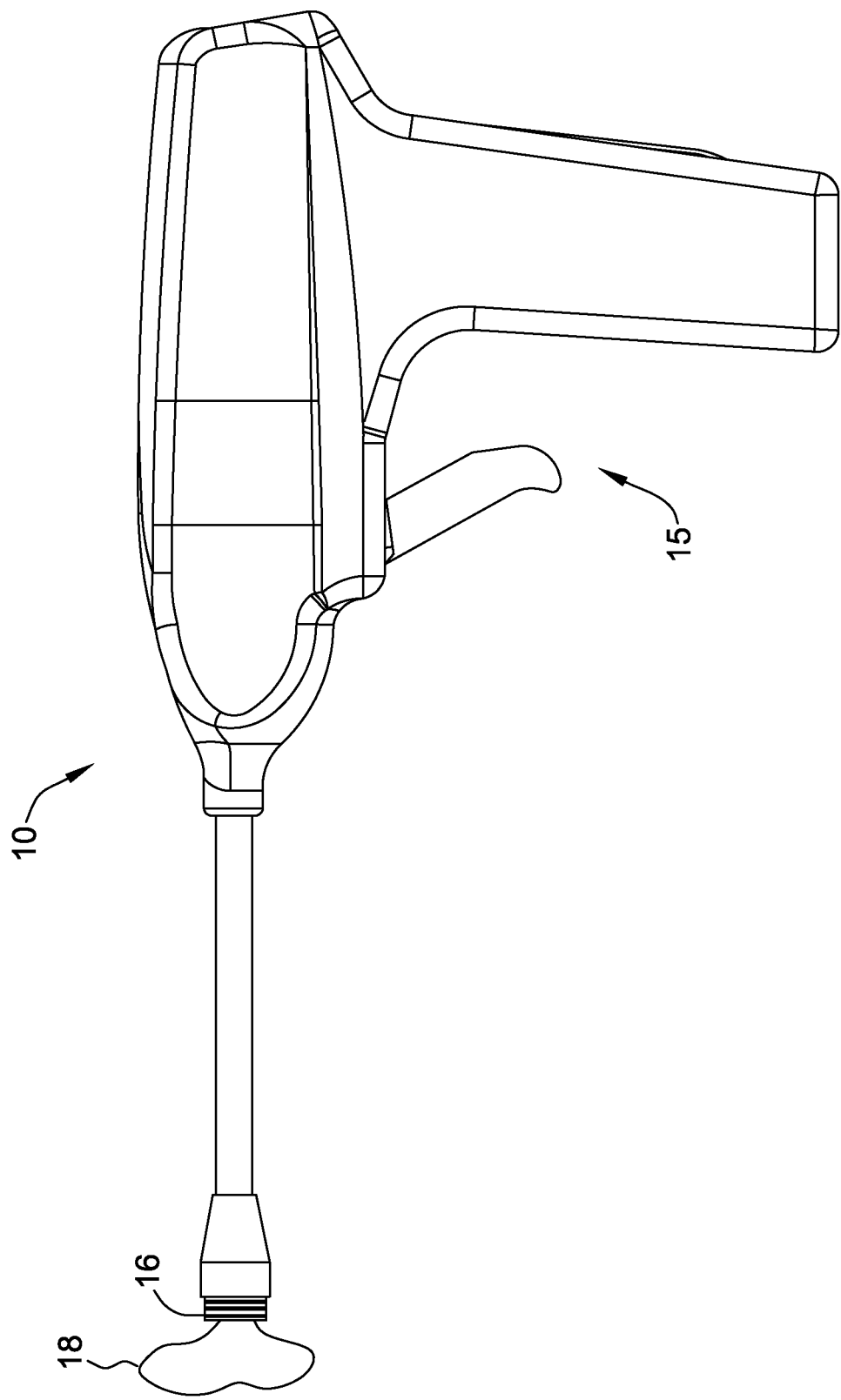
FIG. 3 is a side view of the ligator device shown in FIG. 1 in an third operating position.

FIG. 1 is a side view of a ligator device 10 in a first operating position 12. FIG. 2 is another side view of ligator device 10 in a second operating position 14. FIG. 3 is a side view of ligator device 10 shown in a third operating position 15. Ligator device 10 is configured to contain at least one band 16, to draw a tissue 18 toward band 16 to and to discharge band 16 onto and/or around tissue 18. In the exemplary embodiment, tissue 18 includes a hemorrhoid. Alternatively, tissue 18 may include other body tissues such as, but not limited, esophageal and gastric varices and other venous areas. In second operating position 14, ligator device 10 is configured to draw tissue 18 within ligator device 10 and in third operating position 15, ligator device 10 is configured to discharge band 16 onto tissue 18. In the exemplary embodiment, ligator device 10 is made of plastic materials, either clear or opaque plastic. Alternatively, ligator device 10 can be made of metal such as, but not limited to, stainless steel. Alternatively, ligator device 10 may include any material such as sterilized, hospital grade materials that enables ligator device 10 to function as described herein. In the exemplary embodiment, ligator device 10 is disposable. Alternatively, ligator device 10 is capable of being sterilized after each use for repeated use.

Figure 4:
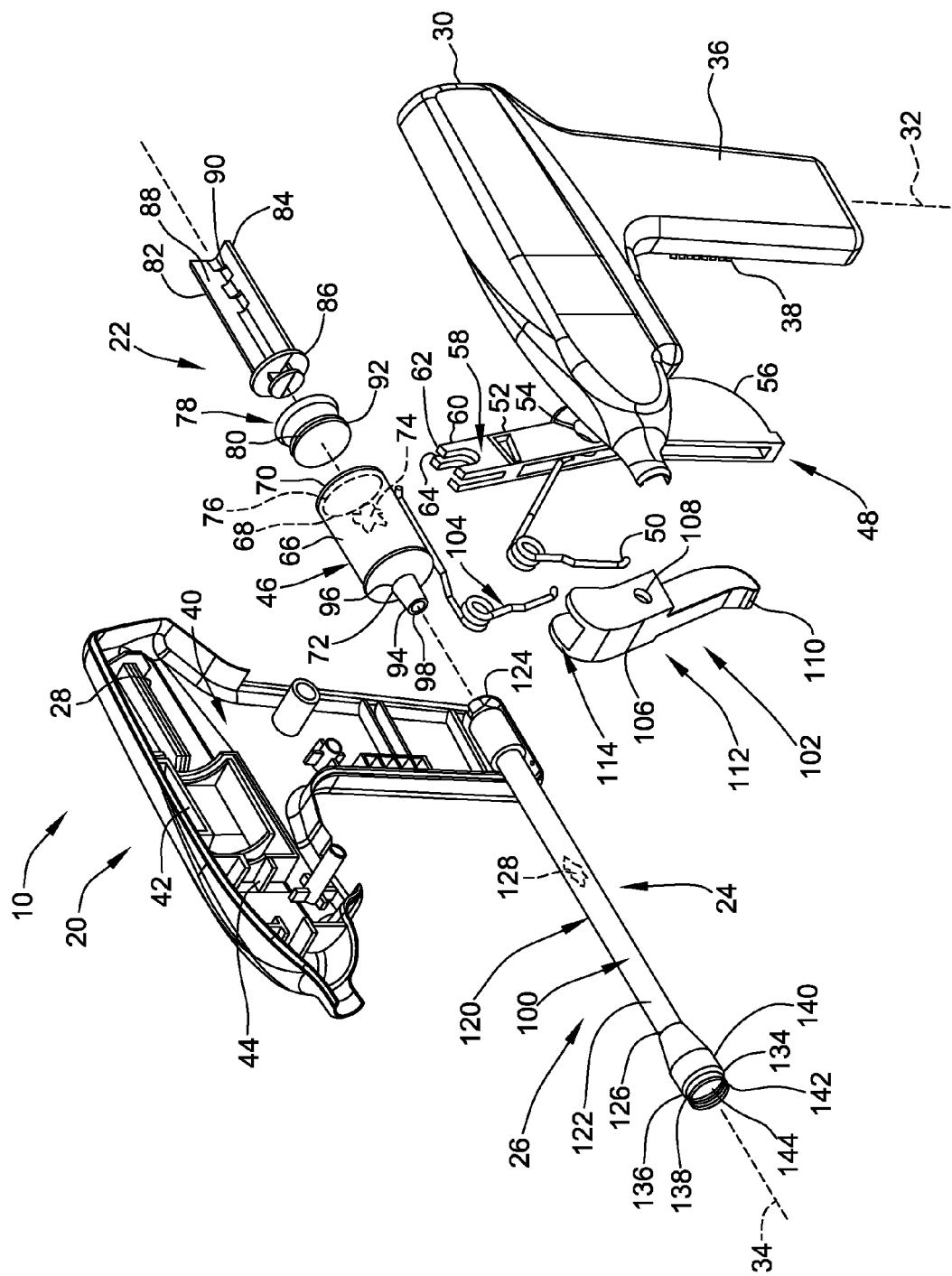
FIG. 4 is a perspective exploded view of the ligator device illustrating a housing assembly, a suction assembly, a dispensing assembly and a discharge assembly.

FIG. 4 is a perspective exploded view of ligator device 10 having a housing assembly 20, a suction assembly 22, a dispensing assembly 24 and a discharge assembly 26. Housing assembly 20 includes a first side 28 and a second side 30 coupled thereto, wherein first and second sides 28 and 30 define a longitudinal axis 32 and a lateral axis 34. Housing assembly 20 further includes a handle 36 having a grip 38 coupled to first side 28 and second side 30. Moreover, first side 28 and second side 30 define an interior space 40. Housing assembly 20 includes a suction support 42 and a dispensing support 44 coupled to first side 28 and/or second side 30 and positioned within interior space 40.

Suction assembly 22 includes a tube 46, a first actuator 48 and a first bias 50, wherein first actuator 48 includes a first trigger 52 and a first pivot 54. First trigger 52 includes an arcuate surface 56 that is sized and shaped to ergonomically receive and contact the user's palm (not shown). Moreover, first trigger 52 further includes a slotted end 58 having a connector 60 extending therefrom. In the exemplary embodiment, connector 60 includes a plurality of prongs 62 separated by a u-shaped cut-out 64. First bias 50 includes a spring. Alternatively, first bias 50 can include any force mechanism to enable suction assembly 22 to function as described herein. Moreover, tube 46 includes an outer side 66, an inner side 68, an open end 70 and partially-open end 72, wherein inner side 68 defines a channel 74 between open end 70 and partially-open end 72. Open end 70 includes a flange 76 coupled to inner side 68 and configured to radially extend inward from inner side 68 and toward channel 74. Flange 76 includes an inner diameter positioned within channel 74.

Suction assembly 22 further includes a plunger 78 configured to reciprocate within channel 74. Plunger 78 includes a sealing head 80 and a piston 82 coupled thereto. Piston 82 includes a first end 84, a second end 86 and a body 88 located between first end 84 and second end 86. Body 88 includes at least one aperture 90 configured to receive first trigger connector 60. Sealing head 80 includes a flange 92, wherein flange 92 includes an outer diameter that is larger than inner diameter of tube flange 76. Moreover, suction assembly 22 includes an interface member 94 coupled to partially-open end 72 and in flow communication to channel 74. In the exemplary embodiment, interface member 94 is tapered from a first end 96 to a second end 98. Alternatively, interface member 94 can be non-tapered. Interface member 94 can include any shape to enable suction assembly 22 to function as described herein.

Dispensing assembly 24 includes a tube 100, a second actuator 102 and a second bias 104, wherein second actuator 102 includes a second trigger 106 and second pivot 108. Second trigger 106 includes an arcuate surface 110 sized and shaped to ergonomically receive and contact a user's finger (not shown). Moreover, second trigger 106 further includes an end 112 having a connector 114 extending therefrom. In the exemplary embodiment, connector 114 includes a fastener such as but not limited to, a weld, an adhesive, a coupler and a collared connector. Any fastener may be used to enable second trigger 106 to couple to dispensing tube 100. In the exemplary embodiment, second bias 104 includes a spring. Alternatively, second bias 104 may include any force mechanism to enable dispensing assembly 24 to function as described herein. Tube 100 includes an outer side 120, an inner side 122, a first open end 124 and a second open end 126, wherein inner side 122 defines a channel 128. First open end 124 is configured to couple in flow communication to second end 98 of interface member 94. More particularly, first open end 124 is configured to pressurably insert within interface second end 98. Alternatively, interface second end 98 can insert within first open end 124 of tube 100. Channel 128 of dispensing tube 100 is coupled in flow communication to channel 74 of suction tube 46 via interface member 94.

Discharge assembly 26 is coupled to dispensing assembly 24. In the exemplary embodiment, discharge assembly 26 is integral with dispensing assembly 24. Alternatively, discharge assembly 26 is removably coupled to dispensing assembly 24 via a fitting (not shown) such as, but not limited to, a quick-disconnect fitting, threaded fitting and/or bushing. Discharge assembly 26 includes a tube 134 having an outer side 136, an inner side 138, an end 140 and a discharge end 142, wherein inner side 138 defines a channel 144 between end 140 and discharge end 142. Discharge channel 144 is coupled in flow communication with channel 128 of dispensing assembly 24.

Figure 5A:
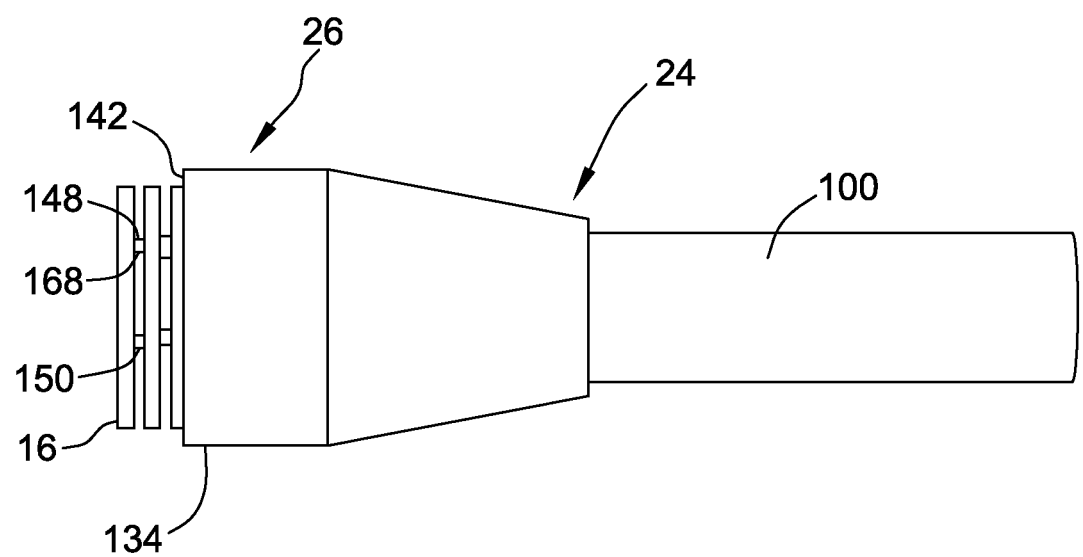
FIGS. 5a, 5b and 5c are cross sectional views of the discharge assembly and a band being discharged onto a tissue.
Figure 5B:
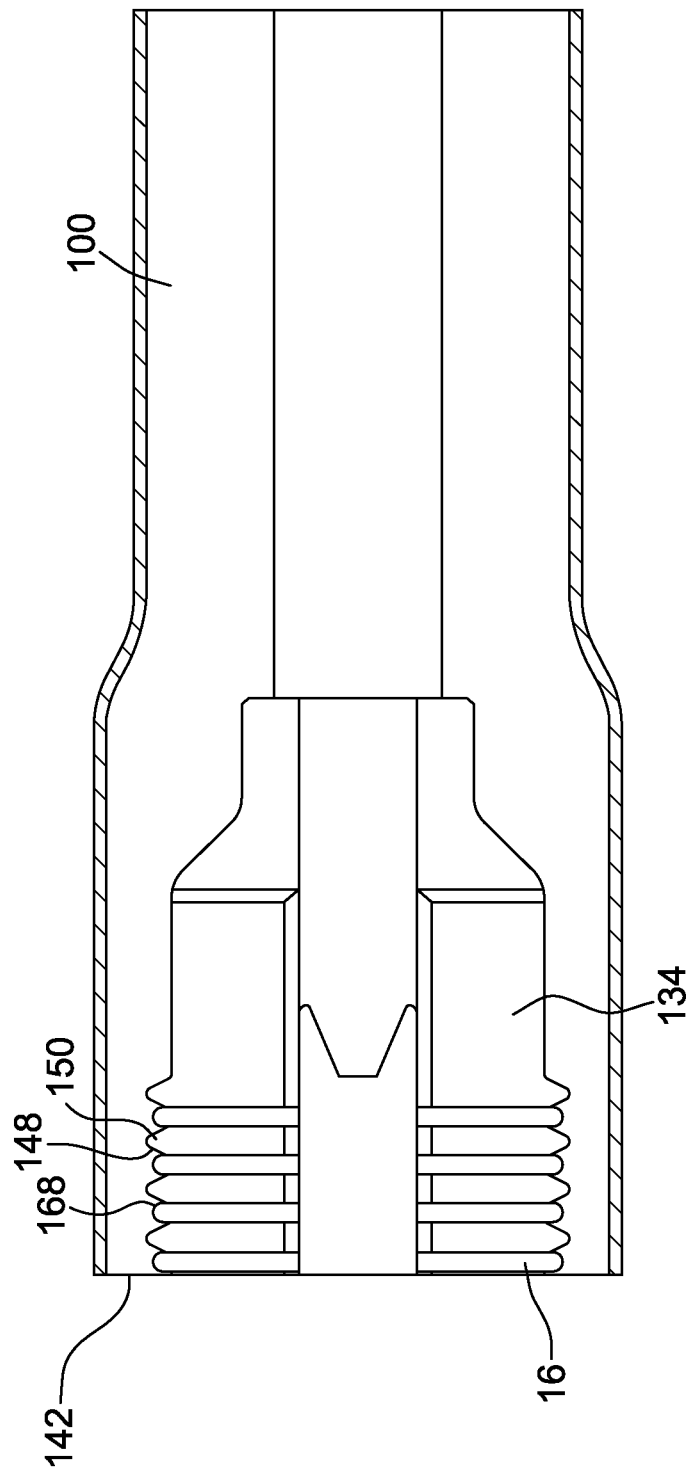
Figure 5C:
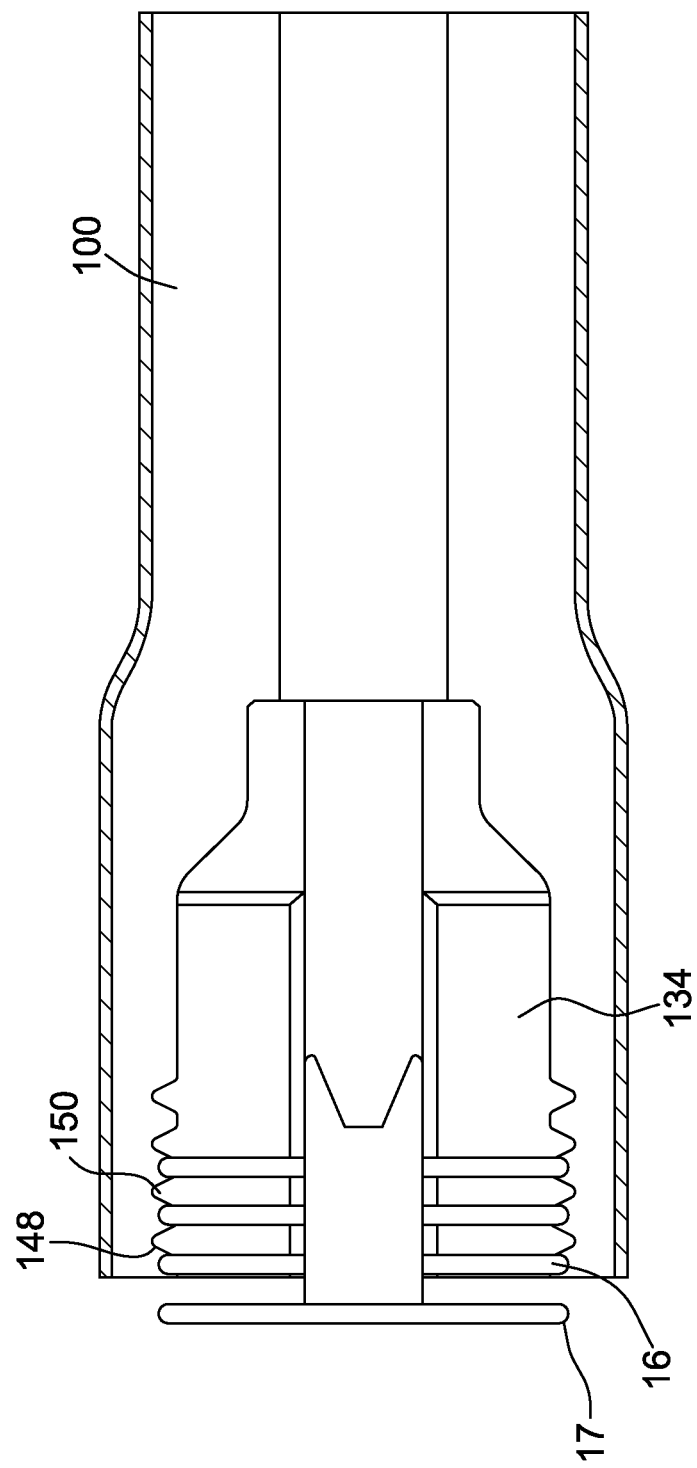

FIG. 5a is a side view of discharge assembly 26 coupled to dispensing assembly 24, wherein bands 16 are coupled to discharge tube 134 and/or dispensing tube 100. FIG. 5b is a side view of another embodiment of discharge assembly 26 coupled to dispensing assembly 24. FIG. 5c is a side view of FIG. 5b of discharge tube 100 advancing along discharge tube 134 to facilitate moving bands 16 along discharge tube 134 and toward discharge end 142. In the exemplary embodiments, dispensing tube 100 includes a plurality of ridges 148 of substantially the same size and shape. Moreover, discharge tube 134 includes a plurality of ridges 150 of substantially the same size and shape.

Ridges 148 and 150 are sized and shaped to accept and removably hold band 16. In the exemplary embodiment, a plurality of ridges 148 and 150 is coupled to hold a plurality of bands 16. Alternatively, ridges 14 and 150 are configured to hold single band 16. Ridges 148 and 150 are approximately aligned to define a plurality of circumferential grooves 168 of substantially the same diameter, each for accommodating a respective elastic band 16 stretched around each groove 168. Although ridges 148 and 152 are shown as having a saw tooth cross-section, ridges 148 and 150 can have a different cross-sections such as, for example rectangular or arcuate, to facilitate advancing bands 16 along discharge assembly 26 and outward discharge end 142. Also, the number of ridges 148 and 150, and hence the number of bands 16 which can be accommodated by the device, can be more or less than four bands 16 shown.

Figure 6:
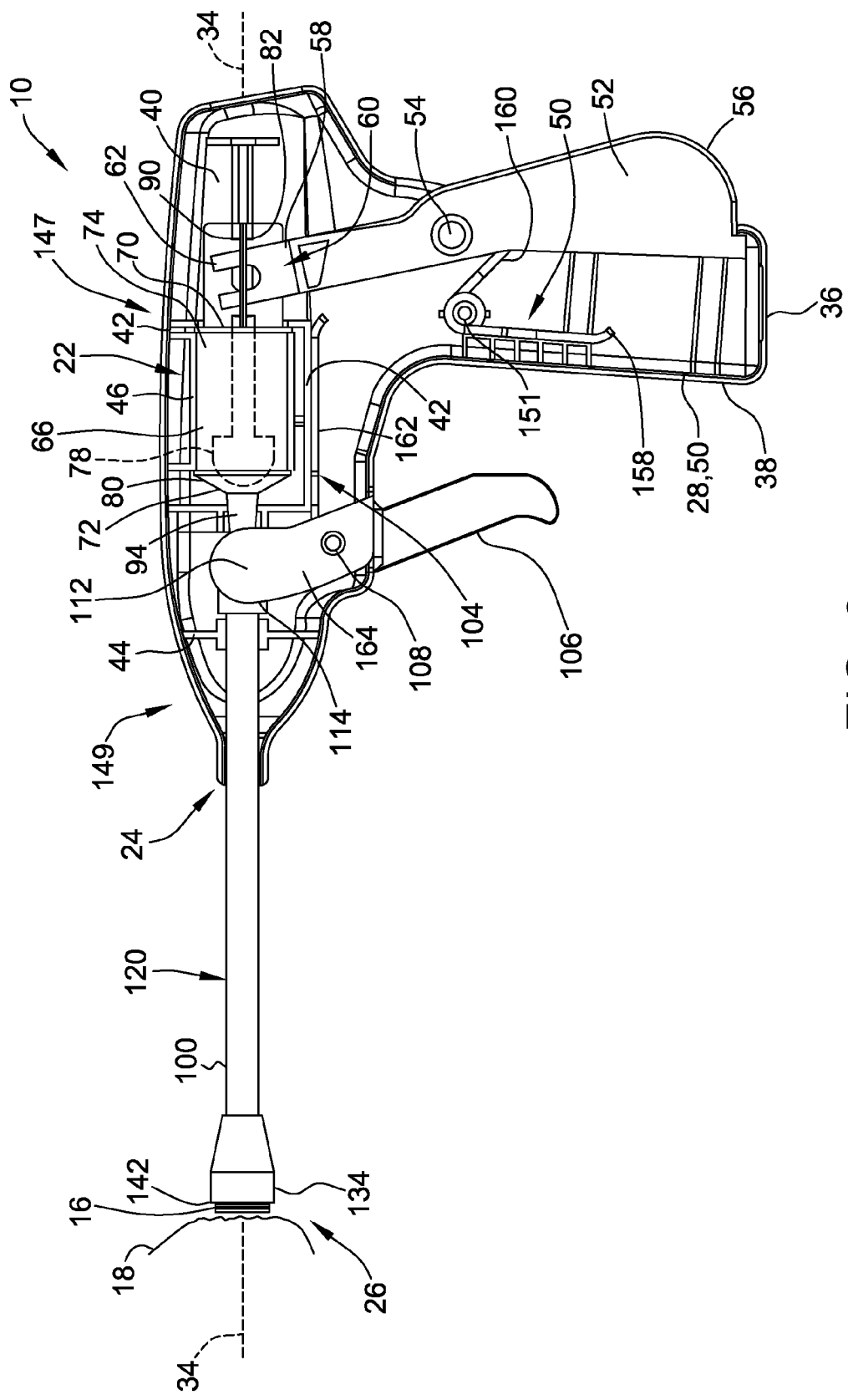
FIG. 6 is a cross sectional view of the ligator device illustrating the suction assembly, shown in FIG. 4, in an extended position, and the dispensing assembly, shown in FIG. 4, in a retracted position.

FIG. 6 is a cross sectional view of ligator device 10 illustrating suction assembly 22 in an extended position 147 and dispensing assembly 24 in a retracted position 149. Suction assembly 22 is coupled to first side 28 and/or second side 30 and within interior space 40 along lateral axis 34. More particularly, outer side 66 of suction tube 46 is coupled to suction supports 42. Further, dispensing assembly 24 is coupled to first side 28 and/or second side 30 and within interior space 40 along lateral axis 34. More particularly, outer side 120 of dispensing tube 100 is coupled to dispensing support 44.

As illustrated, discharge end 142 of discharge assembly 26 is positioned adjacent to tissue 18 and bands 16 are coupled to dispensing assembly 24 and/or discharge assembly 26, for example to ridges 148 and 152 (shown in FIGS. 5a-5c), of dispensing tube 100 and/or discharge tube 134. In the exemplary embodiment, first trigger 52 is coupled to first side 28 and/or second side 30 by first pivot 54, wherein first trigger 52 is configured to rotate about first pivot 54. First bias 50 is coupled to first and/or second sides 28 and 30 about pivot 151, wherein first bias 50 includes a first leg 158 coupled to first side 28 and/or second side 30 and adjacent to grip 38 and includes a second leg 160 coupled to first trigger 52. First leg 158 and second leg 160 are configured to pressure first trigger 52 in extended position 147 wherein arcuate surface 56 of first trigger 52 is positioned outside of handle 36. Moreover, slotted end 58 is coupled to piston 82 through apertures 90. More particularly, connector 60 is configured to extend into and beyond piston apertures 90 to facilitate prongs 62 coupling first trigger 52 to piston 82.

Since first bias 50 is configured to force first trigger 52 in extended position 147, sealing head 80 is positioned in extended position 147. More particularly, under force by first bias 50, slotted end 58 is configured to move counter-clockwise to move piston 82 and facilitate positioning sealing head 80 to couple to partially-open end 72. Sealing head 80 is sized and shaped to match a profile of partially-open end 72. In the exemplary embodiment, sealing head 80 and partially-open end 72 are tapered. Alternatively, sealing head 80 and partially-open end 72 can be non-tapered. Sealing head 80 and partially-open end 72 can include any shape to facilitate forming a fluid seal between interface member 94 and channel 74. Moreover, sealing head 80 is sized and shaped to facilitate providing a suction force or vacuum pressure within tube 46. First trigger 52 is configured to rotate about first pivot 54 and to reciprocally move sealing head 80 within channel 74 between open end 70 and partially-open end 72.

In the exemplary embodiment, dispensing assembly 24 is coupled to first side 28 and/or second side 30 and within interior space 40 along lateral axis 34. More particularly, outer side 120 of tube 100 is coupled to dispensing supports 44. Second trigger 106 is coupled to first side 28 and/or second side 30 by second pivot 108, wherein second trigger 106 is configured to rotate about second pivot 108. Second bias 104 is coupled to second pivot 108, wherein second bias 104 includes a first leg 162 coupled to at least suction support 42 and includes a second leg 164 coupled to second trigger 106. First leg 162 and second leg 164 are configured to pressure second trigger 106 in retracted position 149.

Since second bias 104 is configured to force second trigger 106 in retracted position 149, dispensing tube 100 is positioned in retracted position 149. More particularly, end 112 is configured to move clockwise to move tube 100 toward suction assembly 22. Second trigger 106 is configured to rotate about second pivot 108 and to reciprocally move dispensing tube 100 along lateral axis 34 of housing 20.

Figure 7:
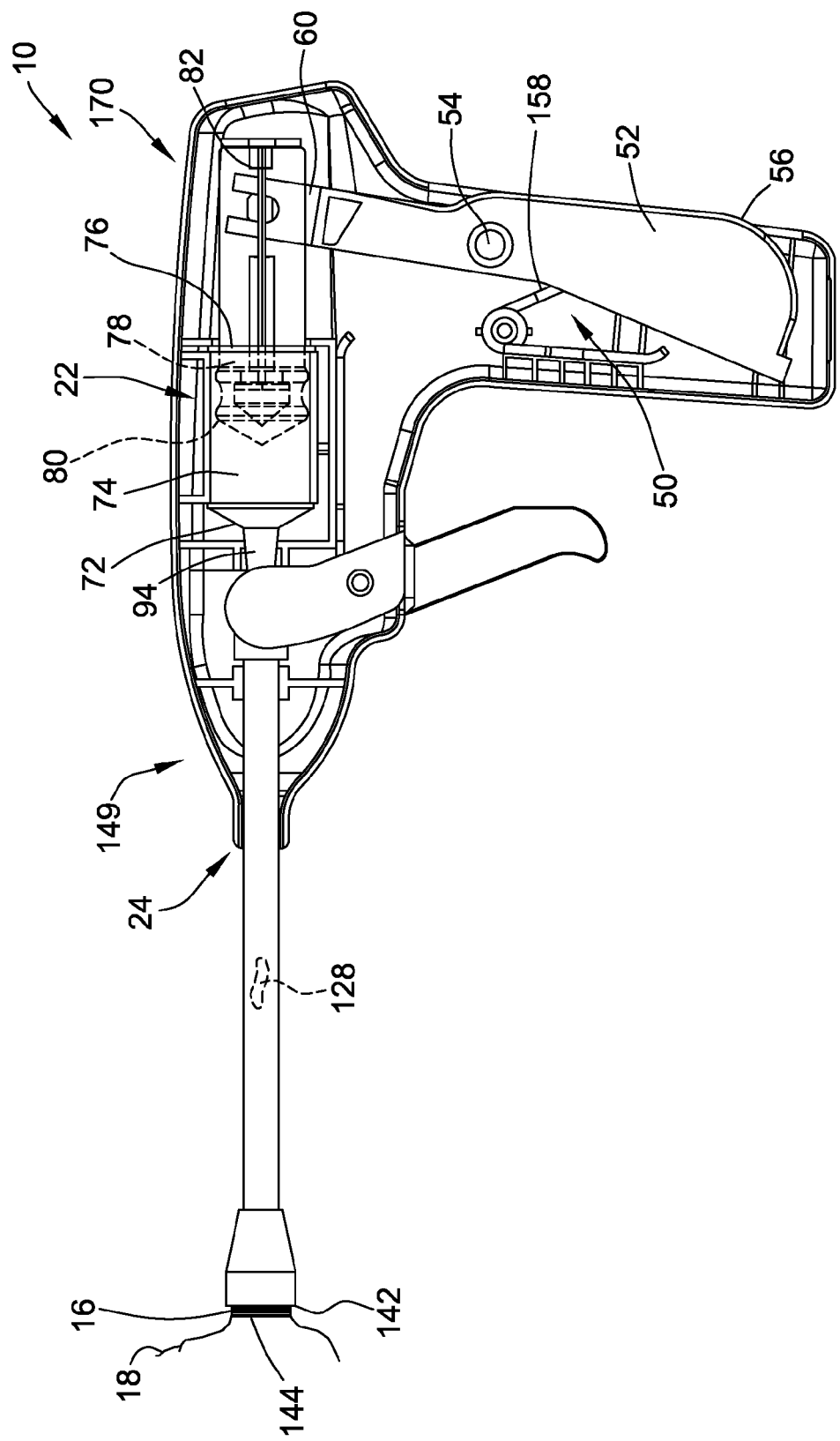
FIG. 7 is a cross sectional view of the ligator device illustrating the suction assembly, shown in FIG. 4, in a retracted position, and the dispensing assembly, shown in FIG. 4, in the retracted position.

FIG. 7 illustrates a cross sectional view of ligator device 10 illustrating suction assembly 22 in a retracted position 170 and dispensing assembly 24 in retracted position 149. Under user force, first trigger 52 is configured to rotate clockwise about first pivot 54 and against second leg 160 of first bias 50. In the exemplary embodiment, at least a portion of arcuate surface 56 is configured to move at least partially inside handle 36. Moreover, connector 60 is configured to move clockwise to move piston 82. Piston 82 is configured to mover plunger 78 from partially-open end 72 toward open end 70. Since outer diameter of sealing head 80 is larger than inner diameter of inner flange 76, sealing head 80 is configured to couple to inner flange 76 to prevent sealing head 80 from moving out of inner tube 46 through open end 70. Since channel 74 of suction assembly 22 is coupled in fluid communication to channel 144 of discharge assembly 26, via dispensing channel 128 and interface member 94, sealing head 80 is configured to create a vacuum pressure within at least discharge channel 144, dispensing channel 128, interface member 94 and suction channel 74. In response to vacuum pressure, tissue 18 is drawn into discharge end 142 and into discharge channel 144.

Figure 8:
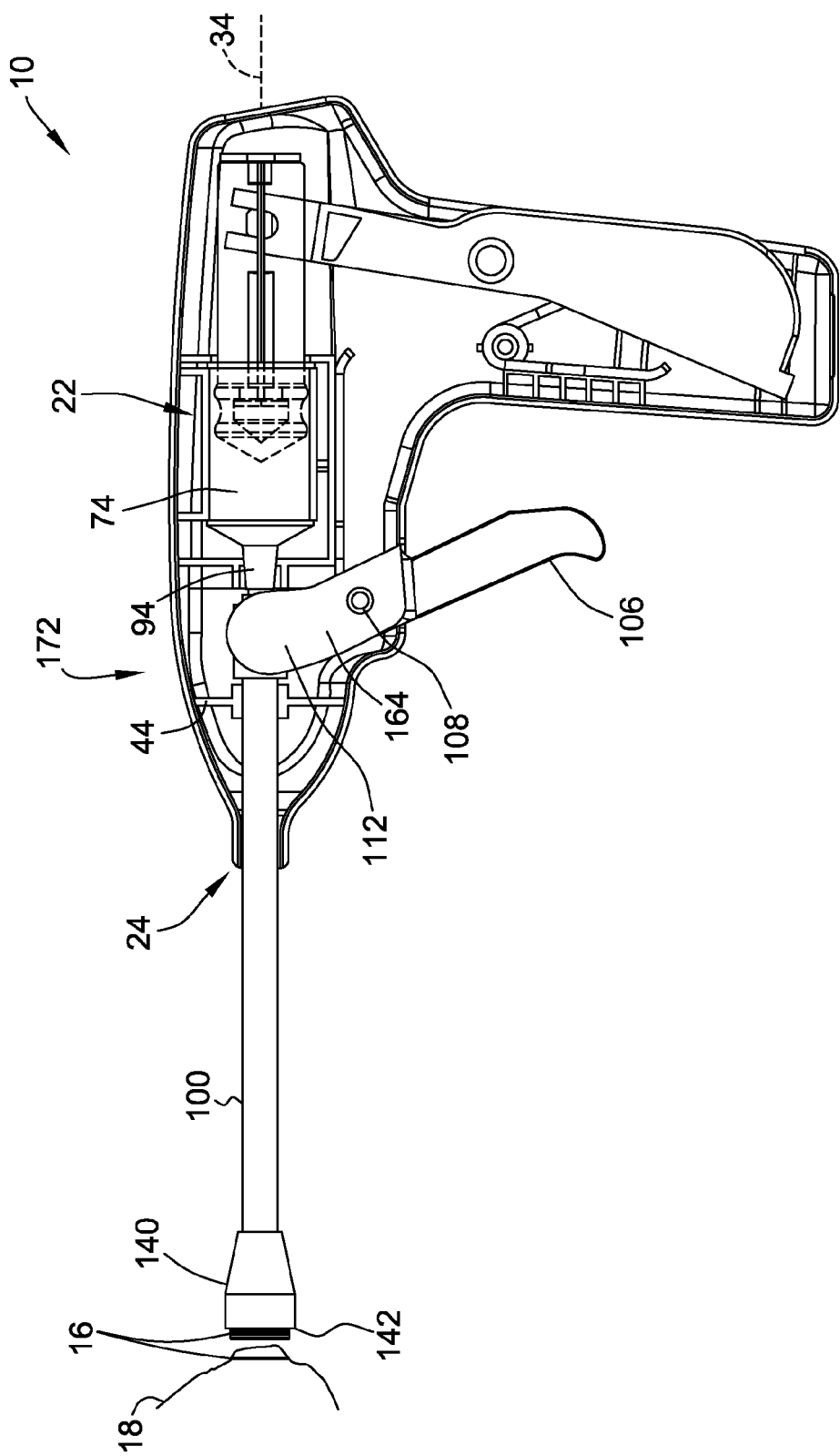
FIG. 8 is a cross sectional view of the ligator device illustrating the suction assembly, shown in FIG. 4, in the retracted position, and the dispensing assembly, shown in FIG. 4, in an extended position.

FIG. 8 illustrates a cross sectional view of ligator device 10 illustrating dispensing assembly 24 in an extended position 172. In the exemplary embodiment, second trigger 106 is configured to rotate counter-clockwise about second pivot 108 and against second leg 164 of second bias 104. In response, end 112 is configured to move dispensing tube 100 along lateral axis 34 and away from suction assembly 22. Dispensing tube 100 remains coupled in flow communication to suction channel 74 via interface member 94. More particularly, since dispensing tube 100 inserts within interface member 94, dispensing tube 100 moves within interface member 94 while remaining coupled in flow communication thereto. Since second trigger 106 is configured to move dispensing tube 100 via coupling of end 112, ridges 148 of dispensing assembly 24 are configured to move with respect to ridges 150 from end 140 toward discharge end 142 to move bands 16 toward tissue 18. Discharge assembly 26 is configured to discharge bands 16 onto tissue 18 as described herein.

In an exemplary operation, bands 16 are stretched around respective grooves 168 of ridges 148, 150 by manual or other means while dispensing tube 100 is in retracted position 149. Discharge assembly 26 is introduced into the anus (not shown) through the use of an anoscope (not shown) to treat, for example, hemorrhoid tissue 18. One hand of user holds the anoscope, while the other hand holds ligator device 10. Alternatively, an anoscope may not be used (known as "blind technique") and the user inserts a finger into patient's anus to locate tissue 18 and to guide ligator device 10 in contact with tissue 18. After identifying the hemorrhoid or other tissue 18 and after discharging end 142 is gently pressed against tissue 18, the user's palm applies force to first trigger 52, and in particular to arcuate surface 56. By pressing and/or pushing arcuate surface 56, first trigger 52 is rotated clockwise about first pivot 54 against the force of first bias 50 to move connector 60 clockwise and to slide plunger 78 from partially-open end 72 and toward open end 70 from extended position 147 to retracted position 170 to facilitate creating vacuum pressure within at least discharge channel 144, dispensing channel 128, interface member 94 and suction channel 74. Tissue 18 is drawn into discharge end 142 via vacuum pressure of suction assembly 22. Moreover, by rotating first trigger 52, at least partially arcuate surface 56 rotates into handle 36.

While holding ligator device 10 at handle 36 and first trigger 52 with one hand, the user applies a finger to operate second trigger 106. In an exemplary operation, by pressing and/or pulling second trigger 106, second trigger 106 is rotated anti-clockwise about pivot 108 against the force of second bias 104 to slide dispensing tube 100 forwardly to extended position 172. To allow for tolerances in manufacture and deformation of parts in use, in retracted position 149 of dispensing tube 100, ridges 148 are slightly to the rear of ridges 150, but not sufficiently to block or interrupt grooves 168. When dispensing tube 100 is moved to extended position 172, ridges 148 have moved forwardly toward discharge end 142 by a distance greater than the pitch of ridges 150. As a result, each band 16 is pushed forwardly by advancing ridges 148 of dispensing tube 100 beyond stationary ridge 150 in front of respective ridge 150 and at the same time the foremost elastic band 16, such as band 17, is pushed off end of discharge end 142 onto tissue 18.

On releasing second trigger 106, second bias 104 is configured to return sliding dispensing tube 100 back to initial retracted position 149. During the return movement of dispensing tube 100, remaining bands 16 beyond ridges 150 to settle back in the grooves 168, bands 16 now each lying one groove 168 nearer discharge end 142. Moreover, on releasing first trigger 52, first bias 50 is configured to return arcuate surface 56 outside of handle 36 and sealing head 80 to initial extended position 147 and couple to partially-open end 72. If another tissue 18 needs to be treated, the procedure is repeated for the number of the bands 16 on discharge assembly 26, without the need to withdraw ligator device 10 from the patient.

Figure 9:
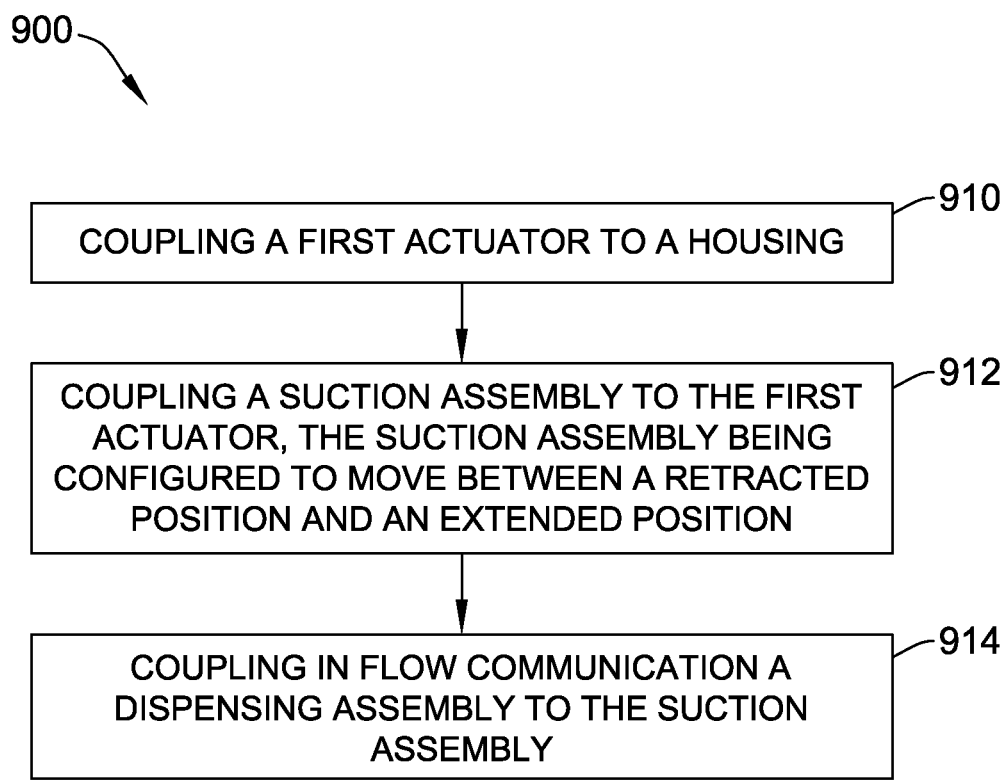
FIG. 9 illustrates an exemplary flowchart illustrating a method of assembling a ligator device.

FIG. 9 illustrates an exemplary flowchart illustrating a method 900 of assembling a ligator device, such as ligator device 10 (shown in FIG. 4). Method 900 includes coupling 910 a first actuator, for example first actuator 48 (shown in FIG. 4) to a housing assembly, such as housing assembly 20 (shown in FIG. 4). Method further includes coupling 912 a suction assembly, for example suction assembly (shown in FIG. 4) to the first actuator. The suction assembly is configured to move between a retracted position, for example retracted position 170 (shown in FIG. 7) to an extended position, for example extended position 147 (shown in FIG. 6). Method 900 includes coupling in flow communication a dispensing assembly, for example dispensing assembly 24 (shown in FIG. 4) to the suction assembly.

In another embodiment (not shown), a cartridge is preloaded with a single band. Alternatively, cartridge is preloaded with multiple bands. The single or multiple preloaded cartridges allow the user choose to use either one band or multiple bands for the procedure. In the exemplary embodiment, the user removably couples either the single loaded cartridge or the multi-loaded cartridge to the dispensing assembly. In an embodiment, the user would attach the appropriate cartridge to discharge end of the ligator and lock the cartridge into place.

In an alternative embodiment (not shown), a powered vacuum source is connected to inner tube to facilitate providing suction force or a vacuum within inner tube to pull tissue within inner tube. Moreover, in an alternative embodiment (not shown), first actuator and second actuator are electronically operated wherein electrical motors are configured to move suction assembly and dispensing assembly.

In the embodiments described herein, ligator device is a device used by a physician to apply latex or latex free elastic bands (O-rings) to the hemorrhoid tissue. Properly placed, these bands cut off the blood supply to the hemorrhoid, causing necrosis, and ultimately the hemorrhoid dies and falls off. In the exemplary embodiment, ligator includes dual-action, reverse pistol grip style, and it requires only one hand to operate. Ligator utilizes an internal plunger mechanism to pull or suck the hemorrhoid tissue into tube of the device to minimize and/or eliminate the need for an external powered, suction method/apparatus. The suction assembly is activated by pushing and/or pulling a trigger. Once the tissue is inside the tip of the device, a firing trigger is pushed and/or pulled and the first band is deployed. The device can be pre-loaded with multiple, such as for example three to four, elastic bands, which will deploy one at a time on to the base of hemorrhoid(s).

In the embodiments described herein, ligator device includes a response device (not shown) to facilitate providing a response such as, but not limited to, an audio response and visual response to indicate predetermined aspects of the procedure. For example, response device facilitates providing a response when the tissue is adequately pulled inside inner tube or when dispensing assembly has adequately dispensed a band and subsequent bands have been adequately advanced. Ligator may include any response that enables ligator to function as described herein. The ligator includes a single handed and dual trigger controlled ligation of tissues to dispense a single band and/or multi bands onto the tissue. The ligator includes a manual suction assembly or an automatic, powered suction assembly.

Exemplary embodiments of systems and methods for using a ligator are described above in detail. The systems and methods are not limited to the specific embodiments described herein, but rather, components of systems and/or steps of the method may be utilized independently and separately from other components and/or steps described herein. The disclosed dimensional ranges include all sub ranges there between. Further, tool may be fabricated from any material that enables tool to function as described herein. Each component and each method step may also be used in combination with other components and/or method steps. Although specific features of various embodiments may be shown in some drawings and not in others, this is for convenience only. Any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A device for discharging at least one band onto a tissue, said device comprising:
    a housing comprising a handle having an axis;
    a suction assembly coupled to said housing;
    a dispensing assembly coupled in flow communication to said suction assembly;
    a first manual actuator coupled to said suction assembly and comprising a surface configured to move said suction assembly between a retracted position and an extended position wherein said suction assembly, in said retracted position, is configured to draw the tissue toward the handle and said surface is partially positioned inside said handle; and
    a second manual actuator coupled to said dispensing assembly and configured to move said dispensing assembly between another retracted position and another extended position wherein said dispensing assembly, in said other extended position, is configured to dispense the at least one band onto the tissue, wherein said first manual actuator and said second manual actuator are substantially parallel to said axis and positioned on opposite sides of said handle.

2. The device of claim 1, wherein said surface is partially positioned outside of said handle when said suction assembly is in said extended position.

3. The device of claim 1, wherein said suction assembly comprises a plunger head and piston rod.

4. The device of claim 1, wherein said suction assembly comprises a plunger head and piston rod and said first manual actuator comprises an end coupled to said piston rod.

5. The device of claim 1, further comprising an interface coupled in flow communication to said suction assembly and to said dispensing assembly.

6. The device of claim 1, wherein said first manual actuator comprises a first trigger having a slotted end.

7. The device of claim 6, wherein said second manual actuator comprises a second trigger.

8. The device of claim 1, further comprising a bias member coupled to said first manual actuator.

9. A device for discharging at least one band onto a tissue, said device comprising:
    a housing comprising a handle having an axis;
    a suction assembly coupled to said housing;
    a dispensing assembly coupled to said suction assembly;
    a discharge assembly coupled in flow communication to said suction assembly;
    a first actuator coupled to said suction assembly and comprising a first trigger having a surface, said first trigger configured to move said suction assembly between a retracted position and an extended position wherein said suction assembly, in said retracted position, is configured to draw the tissue into said discharge assembly and said surface is partially positioned inside said handle; and
    a second actuator coupled to said dispensing assembly and comprising a second trigger, said second trigger configured to move said dispensing assembly between another retracted position and another extended position wherein said dispensing assembly, in said other extended position, is configured to dispense the at least one band along said discharge assembly and onto the tissue, wherein said first actuator and said second actuator are substantially parallel to said axis and positioned on opposite sides of said handle.

10. The device of claim 9, wherein said dispensing assembly comprises a connector that is configured to couple to said second actuator.

11. The device of claim 9, wherein said discharge assembly is configured to couple to a plurality of bands.

12. The device of claim 9, wherein said discharge assembly is removably coupled to said dispensing assembly.

13. The device of claim 9, wherein said surface is partially positioned outside said housing when said suction assembly is in said extended position.

14. A method of assembling a ligator device, said method comprising: coupling a first actuator to a housing comprising a handle having an axis; coupling a second actuator to the housing, wherein the first actuator and the second actuator to the housing, wherein the first actuator and the second actuator are substantially parallel to the axis and positioned on opposite sides of the handle; coupling a suction assembly to the first actuator, the suction assembly being configured to move between a retracted position and an extended position; and coupling in flow communication a dispensing assembly to the suction assembly, is configured to draw the tissue toward the handle and said surface is partially positioned inside said handle; and a second manual actuator coupled to said dispensing assembly and configured to move said dispensing assembly between another retracted position and another extended position wherein said dispensing assembly, in said other extended position, is configured to dispense the at least one band onto the tissue, wherein said first manual actuator and said second manual actuator are substantially parallel to said axis and positioned on opposite sides of said handle.

15. The method of claim 14, further comprising coupling a slotted end of the first actuator to the suction assembly.

16. The method of claim 14, further comprising coupling the second actuator to the dispensing assembly.

* * * * *